United States Patent [19]
Cros et al.

[11] Patent Number: 5,231,016
[45] Date of Patent: Jul. 27, 1993

[54] MICROBIOLOGICAL PRODUCTION OF ITACONIC ACID

[75] Inventors: Patrick Cros; Didier Schneider, both of Melle, France

[73] Assignee: Rhone-Poulenc Chimie, Courbevoie, France

[21] Appl. No.: 855,470

[22] Filed: Mar. 23, 1992

Related U.S. Application Data

[63] Continuation of Ser. No. 346,218, May 2, 1989, abandoned.

[30] Foreign Application Priority Data

May 2, 1988 [FR] France .................... 88 05847

[51] Int. Cl.⁵ .................... C12P 7/44; C12R 1/66
[52] U.S. Cl. .................... 435/142; 435/171; 435/913
[58] Field of Search .................... 435/142, 913, 171

[56] References Cited

U.S. PATENT DOCUMENTS

| | | | |
|---|---|---|---|
| 2,385,283 | 9/1945 | Kane et al. | 435/145 |
| 2,462,981 | 3/1949 | Lockwood et al. | 435/145 |
| 2,567,173 | 10/1953 | Pfeifer et al. | 435/145 |
| 3,044,941 | 7/1962 | Nubel et al. | 435/145 |
| 3,078,217 | 2/1963 | Batti et al. | 435/145 |
| 3,873,425 | 3/1975 | Kobayashi et al. | 435/145 |
| 4,740,464 | 4/1988 | Holdom et al. | 435/144 |

FOREIGN PATENT DOCUMENTS

| | | | |
|---|---|---|---|
| 0034017 | 3/1980 | Japan | 435/145 |
| 0063190 | 4/1984 | Japan | 435/145 |
| 0145718 | 3/1980 | U.S.S.R. | 435/145 |
| 950570 | 2/1964 | United Kingdom | 435/145 |

OTHER PUBLICATIONS

Derwent Abstract 84-125008/20 J59063190/Wata Kagaku Kogyo Apr. 1984.
Derwent Abstract 81-03261D/03 SU-732379 Petukhov et al. May 1980.
Derwent Abs WO8704465 Bjurenvall et al. Jul. 1987.
Derwent Abs WO8701725 Tramwern et al. Mar. 1987.
Chemical Abstract 105: 96032W, "Continuous production of glucoamylase and itaconic acid using an immobilized cell bioreactor with intermitten, air and liquid contacting".

*Primary Examiner*—Herbert J. Lilling
*Attorney, Agent, or Firm*—Burns, Doane, Swecker & Mathis

[57] ABSTRACT

Itaconic acid is produced economically, with high productivity, by microbiologically fermenting an aqueous nutritive medium containing at least one starch as a source of assimilable carbon, in the presence of at least one saccharifying amylolytic enzyme.

13 Claims, No Drawings

MICROBIOLOGICAL PRODUCTION OF ITACONIC ACID

This application is a continuation of application Ser. No. 07/346,218, filed May 2, 1989, now abandoned.

BACKGROUND OF THE INVENTION

1. Field of the Invention

The present invention relates to the production of itaconic acid by the microbial fermentation of carbohydrates, and, more especially, by a microbiological process comprising the conversion of sugars derived from starch.

2. Description of the Prior Art

The synthesis of organic acids by the fermentation of sugars in the presence of appropriate microorganisms has long been known to this art. Typical acids prepared by microbial fermentation include, in particular, acetic acid, lactic acid, citric acid, gluconic and 2-ketogluconic acids, fumaric acid, and itaconic acid. These acids are useful in the food, pharmaceutical, chemical and other industries. Such preparative processes are described, for example, in the text, *Chemicals by Fermentation*, S. J. Gutcho, Noyes Data Corporation (1973).

In industrial fermentations, the selection of the carbon source is based on its availability, its cost and its ability to permit high productivity. Starch is often specified as an inexpensive source of carbon. However, not all microorganisms are capable of metabolizing starch, while the majority metabolize dextrose. Consequently, the starch must be hydrolyzed/saccharified prior to fermentation. Overall production is thereby markedly reduced.

SUMMARY OF THE INVENTION

Accordingly, a major object of the present invention is the provision of an improved and economical fermentation process for the production of itaconic acid wherein starch is used as the source of nutritive carbon, and which improved process has a productivity at least equal to that obtained using glucose or starch hydrolysates rich in glucose.

Briefly, the present invention features the production of itaconic acid by a fermentation process utilizing microorganisms that simultaneously effect an enzymatic hydrolysis of starch.

DETAILED DESCRIPTION OF THE PREFERRED EMBODIMENTS OF THE INVENTION

More particularly according to the present invention, in addition to the saving of time resulting from the elimination of the preliminary stage of saccharification of the starch, the speed of production, surprisingly, is not adversely affected relative to the use of a glucose substrate, even if the fermentation conditions (pH and temperature) are other than optimal with respect to the activity of the hydrolyzing enzyme.

According to the present invention, itaconic acid is produced by the microbial fermentation of an aqueous nutritive medium containing starch as the source of assimilable carbon, such fermentation being carried out in the additional presence of at least one saccharifying amylolytic enzyme.

The starch used as the source of carbon according to this invention may be any cereal starch, such as wheat starch, corn starch, sorghum starch, rice, tapioca, rye, oats starch, or a starch of tubers, such as potato starch.

The starch may be used in the crude (raw), liquefied or partially saccharified state. By the term "starch" is intended any raw starch in an aqueous dispersion and the starch hydrolysates resulting from an incomplete hydrolysis of starch, such as fluidized starch, starch syrups and hydrolysates rich in dextrose. Starch hydrolysates differ from each other by their degree of hydrolysis, expressed dextrose equivalents D.E., and their higher oligosaccharide and polysaccharide contents. Fluidized starches have a D.E. ranging from about 3 to 20 and generally contain 50% to 95% polysaccharides, and a degree of polymerization higher than G 7 (7 glucose units). The starch syrups or glucose syrups with low dextrose equivalents have a D.E. ranging from approximately 20 to 68 with 10% to 50% polysaccharides having a degree of polymerization higher than G 7. Starch hydrolysates or syrups rich in dextrose have a D.E. of up to 90% to 98%. The preparation of the starch hydrolysates is well known to this art. Conventionally, fluidized starches and starch syrups are produced by acid and/or enzymatic hydrolysis utilizing a liquefaction $\alpha$-amylase, optionally followed by a $\beta$-amylase. For hydrolysates rich in glucose, the starch is most typically converted in a two-stage process, by the action of a saccharification enzyme, such as glucoamylase, also known as amyloglucosidase.

In the actual practice of the process according to the invention, a starch syrup is preferably used, and even more preferably a fluidized starch. The use of hydrolysates rich in glucose is of little interest from an economic standpoint, as such procedure requires a preliminary saccharification step, which is a lengthy stage, even under maximal amyloglucosidase conditions (generally attained at a temperature greater than 50° C. and at a pH of from 4.5 to 5).

Starch and its products of hydrolysis may be directly used in the process of the invention in unpurified state, after sterilization. Naturally, purified, concentrated or dehydrated commercial products, such as maltodextrins, may also be used.

The starch is present in the fermentation medium in amounts necessary to yield 1% to 15% by weight glucose relative to the fermentation medium. Expressed as raw starch, on a dry solids basis, suitable such amounts may range from 10 to 160 g/l, preferably from 60 to 140 g/l of the fermentation medium.

The amylolytic saccharification enzymes which are added according to the invention to the fermenting medium containing the itaconic acid producing microorganisms, are capable of converting the dextrins of the starch into glucose and maltose. Representative saccharification enzymes are the saccharifying $\alpha$-amylases, such as the $\alpha$-amylase of *Bacillus subtilis var.amylosaccharitiens*, the fungal $\alpha$-amylase, the $\beta$-amylases, glucoamylase, isoamylase and pullulanase. These enzymes may be used either alone or as mixtures thereof.

Preferably, glucoamylase is used, in light of its high specificity. The glucoamylase may entirely be a fungal glucoamylase, such as those of the genera *Aspergillus, Endomyces or Rhizopus*. In the particular case in which raw starch is used as the carbon source, it is also possible to use a liquefying enzyme in addition to the saccharifying enzyme, for example a mixture of a liquefying $\alpha$-amylase/$\beta$-amylase, or of a liquefying $\alpha$-amylase/glucoamylase. Industrial enzymatic preparations are described in *Encyclopedia of Polymer Science*, Vol. 6, pp 46–53 (1967).

The amylolytic saccharifying enzyme, and optionally the liquefying enzyme, are added to the fermenting medium in amounts necessary to carry out the saccharification and fluidizing, respectively, of the starch. The minimum amount that may be used is a function of the activity of the enzyme, the amount and D.E. of the starch present in the medium, and is determined readily by one skilled in this art. In general, amounts are added sufficient to yield 0.04 to 2 units of enzymatic activity, preferably 0.1 to 1 unit, per gram of starch (expressed as dry solids content). For example, the saccharifying enzyme, AMG 200L ®, marketed by Novo Industry, which is a glucoamylase, may be added in an amount of 0.02% to 1%, preferably 0.05% to 0.5% by weight, based on the weight of the solids contained in the liquefied starch present in the fermenting medium.

Any microorganism capable of producing itaconic acid in the presence of sugars may be employed in the process of the invention. Fungi of the species *Aspergillus itaconicus* and *Aspergillus terreus* are particularly representative, with the latter being the preferred.

In addition to the source of carbon and the amylolytic enzyme according to the invention, the production medium and the fermentation conditions may be selected from among those abundantly described in the literature.

The source of nitrogen, in particular, may be selected from among metabolizable organic and/or inorganic compounds, such as soluble extracts of corn (CSL) and/or soybeans, urea, ammonium sulfate, ammonium chloride, ammonium phosphate, ammonium nitrate, and the like, and mixtures thereof. The medium may also contain inorganic salts, such as the sulfates, chlorides, phosphates of Ca, Mg, Na, K, Fe, Ni, Co, Cu, Mn, Zn, together with other conventional additives, such as agents to control the pH and/or antifoaming agents.

The microorganism is introduced into the fermentation medium in known manner, either by inoculation or by means of intermediate cultures.

The amylolytic enzyme is preferably added in the sterile medium immediately prior to inoculation. Fermentation is conveniently carried out at an acid pH ranging from approximately 1.8 to 5, and at a temperature of from approximately 20° to approximately 40° C., with the optimal conditions depending on the particular strain of the microorganism employed. High itaconic acid percentages were obtained by using *Aspergillus terreus* at a pH preferably ranging from 2 to 4 and even more preferably from 2 to 3.4, with the temperature being maintained at about 30° to 40° C.

After the fermentation has been carried out, the itaconic acid produced may be recovered from the wort and purified by known techniques, such as filtering, concentration, crystallization or solvent extraction.

It will of course be appreciated that the above description refers to a specific process for the preparation of itaconic acid by the microbial fermentation of a medium containing a carbohydrate source produced from starch, in the presence of enzymes capable of hydrolyzing starch or degradation products thereof into mono- or disaccharides, and that the invention itself is not limited to the precise composition of the fermentation medium or to the particular processing parameters.

In order to further illustrate the present invention and the advantages thereof, the following specific examples are given, it being understood that same are intended only as illustrative and in nowise limitative.

EXAMPLE 1

Preparation of crude fluidized starch

An aqueous solution of wheat starch having 350 g/l of dry solids was homogenized, the pH adjusted to 6.5 and 0.175 g/l of liquefying enzyme (TERMANYL 120L ®, marketed by Novo Industry) was added. The solution was introduced into a steam injection sterilizer. The temperature was maintained at 100° to 105° C. for 7 min, cooled to 95° C. and maintained at this temperature for 2 hours in an agitated tank, then cooled to 35° C.

Fermentation

The fluidized starch solution containing 130 kg of dry solids was introduced into a 1,400 l fermenter. The following materials were added thereto:

(i) a nutritive solution sterilized for 30 min at 100° C., containing 0.5 kg corn extract, 3.45 kg magnesium chloride, 0.3 kg magnesium sulfate, 0.9 kg urea, 0.4 kg sodium chloride, 0.033 kg zinc sulfate, 0.05 kg monopotassium phosphate, 1 kg calcium chloride, 0.06 kg copper sulfate and 0.3 kg sulfuric acid (the pH was 3.6);

(ii) 0.29 kg amyloglucosidase (AMG 200L ®, marketed by Novo Industry).

This production medium, the final volume of which was adjusted to 1,000 l, was agitated, aerated and inoculated with 20 l of an *Aspergillus terreus* NRRL 1960, aged 35 hours, prepared at 32° to 35° C. in a fermenter containing 25 g/l glucose, 4.5 g/l magnesium sulfate, 0.4 g/l sodium chloride, 0.004 g/l zinc sulfate, 0.1 g/l monopotassium phosphate, 0.5 g/l corn extract, 2.0 ammonium nitrate and 0.5 g/l sulfuric acid.

The temperature of the medium was controlled at 32° to 35° C.

Fermentation was terminate after the sugar was consumed and when the acidity was maximal and stable.

Wort samples were periodically withdrawn to evaluate the itaconic acid content, determined by high performance liquid chromatography.

Analysis of samples periodically withdrawn over the course of the fermentation gave the following results:

| Duration of fermentation (hours) | Accumulated itaconic acid (g/l) |
|---|---|
| 18 | 4.55 |
| 24 | 13 |
| 43 | 41.6 |
| 75 | 70.3 |

The productivity was 0.937 g/l.h.

EXAMPLE 2

Comparative

A fermentation was carried out as in Example 1 using the same culture of *Aspergillus terreus*. The production medium was identical, except that no glucoamylase was added and that the liquefied starch was replaced by the same amount (expressed in solids content) of a starch hydrolysate previously obtained by enzymatic saccharification by the following process:

Following the liquefaction of the starch carried out in the manner indicated in Example 1, the solution was cooled to 60° C., adjusted to pH 4.5, and 168.4 g amyloglucosidase AMG 200L ® were added thereto. It was then maintained at 60° C. for 60 hours. The solution (DE≧96) was cooled to 30° to 35° C. and introduced into the fermenter.

After the addition of the nutritive solution, the medium was inoculated and fermentation carried out under the conditions of Example 1. The fermentation was discontinued following the exhaustion of the glucose and when the acidity was at a maximum and stable value.

Analysis of the samples periodically withdrawn gave the following results:

| Duration of fermentation (hours) | Itaconic acid accumulated (g/l) |
|---|---|
| 18 | 0.65 |
| 43 | 26.65 |
| 66 | 61.7 |
| 85 | 74.35 |

Productivity was 0.874 g/l.h.

EXAMPLE 3

Comparative

A fermentation was carried out as in Example 1, but in the absence of amyloglucosidase and by replacing the fluidized starch with 150 kg purified glucose syrup having a dry solids content of 74% and a DE of 96-98, marketed by the Roquette Co.

Analysis of samples periodically withdrawn over the course of the fermentation gave the following results:

| Duration of fermentation (hours) | Itaconic acid accumulated (g/l) |
|---|---|
| 23 | 3.25 |
| 41 | 18.2 |
| 64 | 43.5 |
| 94 | 64.35 |

The productivity was 0.684 g/l.h.

EXAMPLE 4

Experiment A

Comparative

Into an aerated and agitated fermenter, 30 l of a solution of liquefied DE 10-15 starch was introduced. This solution was prepared from a solution of 180 g/l of wheat starch, which was homogenized, 4.86 g Termanyl 120L ® enzyme added thereto, its pH adjusted to pH 6.5, and it was then heated to 102° C. over one hour, and finally cooled to 35° C.

A nutritive solution, sterilized for 30 min at 100° C. and containing 25 g corn extract, 172 g magnesium chloride, 15 g magnesium sulfate 7H$_2$O, 45 g urea, 20 g sodium chloride, 1.7 g zinc sulfate, 2.5 g monopotassium phosphate, 50 g calcium chloride, 3 g copper sulfate and 15 g sulfuric acid, was added.

The medium, having a final volume 50 l and a pH of 3.6, was heated to 32° to 35° C. and inoculated with 1 l of an *Aspergillus terreus* NRRL 1960 culture, aged for 35 hours and prepared as described in Example 1.

The fermentation was carried out at 32° to 35° C. under agitation of 200 rpm and a degree of aeration of 2 m$^3$/h, with the pH ranging freely over the course of the fermentation.

The duration of the fermentation was 112 hours. The wort contained 47.5 g/l itaconic acid which constituted a productivity of 0.424 g/l.h.

Experiment B The procedure was conducted as in Experiment A, but prior to the inoculation, 18 g amyloglucosidase AMG 200L ® were added to the production medium.

The duration of the fermentation, carried out under the conditions of Experiment A, was 80 hours. The wort contained 74.1 g/l itaconic acid, which constituted a productivity of 0.926 g/l.h.

EXAMPLES 5 to 9

A series of fermentations as described in Example 4 was carried out by varying the amount of amyloglucosidase added to the medium prior to inoculation with the *Aspergillus terreus* culture.

The results are reported in the following Table:

TABLE

| EXAMPLES: | 5 | 6 | 7 | 8 | 9 |
|---|---|---|---|---|---|
| Liquefied starch g/l (dry solids) | 130 | 130 | 130 | 130 | 130 |
| AMG 200L ® g/l | 0.16 | 0.29 | 0.36 | 0.42 | 0.65 |
| Duration of fermentation h | 90 | 83 | 80 | 78 | 70 |
| Acid produced g/l | 67.3 | 70.9 | 74.1 | 73.3 | 69.6 |
| Yield/glucose equivalents % | 53.3 | 56.2 | 58.7 | 58.1 | 55.3 |
| Productivity g/l.h | 0.747 | 0.854 | 0.926 | 0.94 | 0.99 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for producing itaconic acid comprising microbiologically fermenting an aqueous nutritive medium containing at least one starch as a source of assimilable carbon, where both at least one saccharifying amylolytic enzyme and a microorganism of the species *Aspergillus itaconicus* or *Aspergillus terreus* have been introduced into the medium and further wherein saccharification of the at least one starch to mono- and/or disaccharides by the at least one saccharifying amylolytic enzyme and fermentation of the mono- and/or disaccharides to itaconic acid by the microorganism are performed simultaneously in the nutritive medium, the process further comprising the recovery of itaconic acid from the nutritive medium.

2. The process as defined by claim 1, wherein said at least one starch is in liquefied or partially saccharified state.

3. The process as defined by claim 1, wherein said at least one starch is in a raw state.

4. The process a defined by claim 1, said medium of fermentation further comprising a liquefying enzyme.

5. The process as defined by claim 1, said medium of fermentation comprising such amount of starch as to provide 1% to 15% by weight of glucose.

6. The process as defined by claim 1, said at least one saccharifying amylolytic enzyme comprising an α-amylase, β-amylase, glucoamylase, isoamylase, pullulanase, or mixture thereof.

7. The process as defined by claim 1, wherein the amount of said at least one saccharifying amylolytic enzyme is such as to provide 0.04 to 2 units of enzymatic activity per gram of said at least one starch.

8. The process as defined by claim 7, wherein the amount of said at least one saccharifying amylolytic enzyme is such as to provide 0.1 to 1 unit of enzymatic activity per gram of said at least one starch.

9. The process as defined by claim 1, wherein said at least one saccharifying amylolytic enzyme comprises a glucoamylase.

10. The process as defined by claim 9, wherein the amount of said glucoamylase ranges from 0.02% to 1% by weight, based on the weight of the starch solids.

11. The process as defined by claim 10, said amount of glucoamylase ranging from 0.05% to 0.5% by weight, based on the weight of the starch solids.

12. The process as defined by claim 1, wherein the microbiological fermentation is carried out by a fungal microorganism of the species *Aspergillus terreus*.

13. The process of claim 1 wherein an amylolytic enzyme is added to the nutritive medium prior to the introduction of the microorganism to the medium.

* * * * *